United States Patent [19]

Silvey

[11] Patent Number: 4,829,993

[45] Date of Patent: May 16, 1989

[54] SKIN PROTECTIVE DEVICE AND METHOD

[76] Inventor: William C. Silvey, 1917 N. 44th Ave., Hollywood, Fla. 33021

[21] Appl. No.: 254,610

[22] Filed: Oct. 7, 1988

Related U.S. Application Data

[63] Continuation-in-part of Ser. No. 128,003, Nov. 23, 1987, abandoned.

[51] Int. Cl.$^4$ .............................................. A61F 15/02
[52] U.S. Cl. .................................... 128/91 A; 128/155
[58] Field of Search ...................... 128/91 A, 87 R, 83, 128/82, 155, 156, 157

[56] References Cited

U.S. PATENT DOCUMENTS

| | | | |
|---|---|---|---|
| 2,187,175 | 1/1940 | Prosperi | 128/91 A |
| 2,206,339 | 7/1940 | Ulman, Jr. | 128/91 A |
| 2,230,781 | 2/1941 | Longfellow | 128/91 A |
| 2,299,125 | 10/1942 | Brinkmann | 128/91 A |
| 2,523,837 | 9/1950 | Luger | 128/91 A |
| 3,556,092 | 1/1971 | Eisenberg | 128/87 R |
| 3,985,129 | 10/1976 | Huene | 128/91 A |
| 4,041,941 | 8/1977 | Driver | 128/91 A |

OTHER PUBLICATIONS

The Journal of Bone and Joint Surgery, *A Simple Method of Applying Plaster Casts to Provide for Easy Removal,* 1941, pp. 184–186.
Orthopedic Appliance Atlas, pp. 113, 114, 1952, *Methods of Removing Casts.*

Primary Examiner—Robert A. Hafer
Assistant Examiner—Kevin G. Rooney

[57] ABSTRACT

A skin protective device to be positioned under a bandage to act as a barrier when the bandage is cut away in removal of it. The device is cut to a length somewhat longer than the bandage so that the opposite ends stick out. It is a flat thin bendable barrier strip of severable material having generally parallel side edges and a pair of main surfaces witih a first and a second end. The strip is encased in an envelope secured about the strip main surfaces. Marked along the length of the device on an outer main surface there may be indicia preferably in the form of a line extending longitudinally about midway between the edges so that one may be guided in cutting away a bandage and be certain in the knowledge that the barrier underlies it.

16 Claims, 1 Drawing Sheet

U.S. Patent | May 16, 1989 | 4,829,993
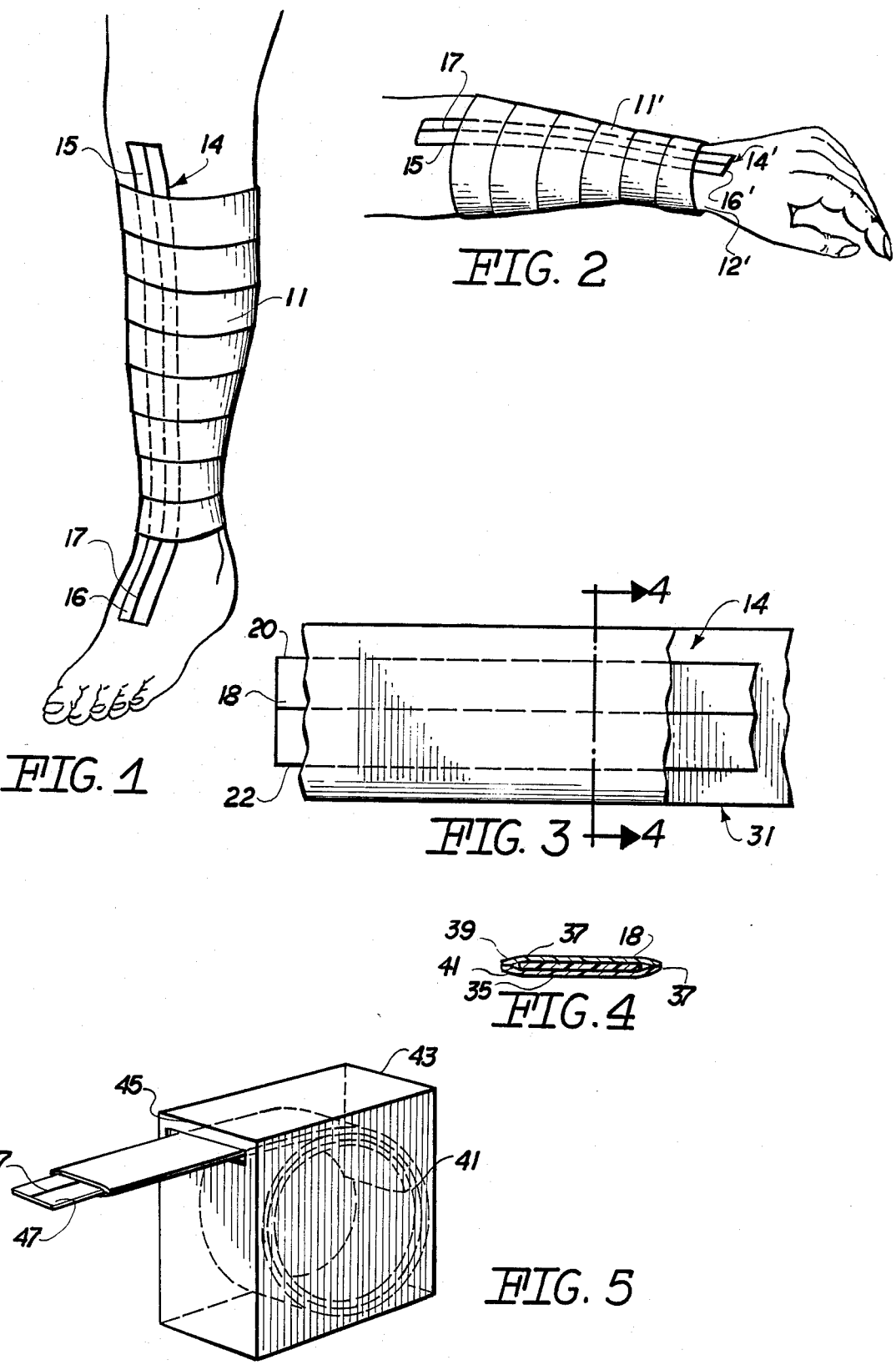

SKIN PROTECTIVE DEVICE AND METHOD

This application is a continuation in part of patent application Ser. No. 128,003 filed 11/23/87, now abandoned.

FIELD OF THE INVENTION

This invention relates to a skin protective device or barrier to be positioned beneath a bandage, and more particularly to a cut resistant strip wrapped beneath a snug fitting bandage to protect the underlying skin when cutting away the bandage with a sharp cutting tool.

BACKGROUND OF THE INVENTION

Certain persons suffer from conditions that require the utilization of tight fitting bandages that enclose the limb, generally the leg. These bandages may be of the type referred to as pressure gradient bandages as exemplified by the Unna boot. For example a diabetic patient or a patient with venous valvular insufficiency may have black and blue legs on which ulcers break out due to impaired circulation. In order to treat such conditions, bandages are used because they produce an improved blood and lymphatic circulation, reduce edema and promote healing. It is generally a thin bandage wrapped relatively tight to cause the blood to flow through the black and blue area which is ulcerated. The bandages are not kept on for weeks until a bone mends but, rather, are removed within a day or two and replaced as required. Such bandages when applied are wet with a medicine and generally harden somewhat. The problem in the past has been that when such types of bandages are removed, the person removing it must spend considerable amounts of time, often up to about one half hour by one of two methods. The first method has been to attempt to put one blade of a scissors beneath the bandage and to cut along the bandage. This it is clear hurts the severely damaged leg of the patient wearing a bandage such as a Unna boot. The other method has been to apply a razor blade to slice the bandage. In this circumstance, it causes nicks to the already damaged flesh of such a bandaged person.

Patients suffering these disorders cannot heal these cuts as easily as others. Furthermore, the skin beneath the bandage may become edematous and swollen so that it is both harder to fit a bandage scissors beneath the bandage and easier to cut into the skin.

Means of addressing the problem of cutting through rigid plaster casts without cutting the underlying skin are taught by U.S. Pat. Nos. 2,187,175; 2,206,339; 2,230,781 and 4,041,941 which provide spaced channels beneath the cast for admission of the cutting tool. U.S. Pat. Nos. 2,299,125 and 2,523,837 provide cutting strips that engage the plaster and cut through the cast when pulled upward. These techniques are not directed to, nor are they particularly effective in the removal of bandages of the type herein discussed.

In the past, various devices have been developed for protecting skin wounds, particularly surgical wounds. However, such devices are generally of the type which are positioned adjacent to the opposite sides of a wound to maintain a bandage out of immediate contact with the skin to prevent the bandage from adhering to the wound and to allow free circulation of air. The present device is not concerned with protecting wounds, burns, cuts, sores or other sensitive areas of the body nor in supporting a bandage above them. Rather, it is concerned with the removal of the bandage without imposing new cuts or injuries to the patient. It is of a barrier which underlies the bandage which is cut so that it is of a length longer than the bandage so that the opposite ends extend from it and wherein a guide indicia is provided so that one may have a sight for manipulating the tool removing the bandage. Examples of prior art protective devices are found in the following U.S. Patents. U.S. Pat. No. 4,134,399 is of a protective device which is used as a shield for a wound or sensitive skin barrier by providing a support for a bandage to be held out of contact with the wound or sensitive skin area. U.S. Pat. No. 3,068,863 is of a patch which is attachable to the face and eyelid of a wearer to protect the eye. The device of U.S. Pat. No. 2,933,083 is of a surgical dressing and reinforcement for treating minor fractures. U.S. Pat. No. 3,304,938 is of a bandage support which is to be positioned at a wound site and to support the bandage above the wound itself.

SUMMARY OF THE INVENTION

It is an object of the invention to provide a simple, inexpensive skin protective device to aid in the removal of a "pressure gradient" type dressing and other types of hard, semi-hard or soft dressings that are so tight that it is difficult to slide a bandage scissors in place.

A further principal object of the invention is to provide such a skin protective device which can be conveniently dispensed and sized for a specific wound or ulcerated or sore area.

Generally, this invention is of a skin protective device which is composed of a strip which can be positioned under a bandage to act as a protective barrier to avoid injury when the bandage is cut away in removing it. It includes a longitudinally extending line to guide the person in cutting the bandage away. The barrier device is especially useful in the removal of compression-type bandages which have been applied in a pressure gradient manner. For example, some bandages are normally quite tight about the skin so that a person with a bandage being cut away is frequently cut by the instrument being used to remove it. This invention provides a barrier which is positioned on the skin beneath the bandage and is in strip form with the end extending outwardly on opposite ends of the bandage. On the barrier device there is a central line or other indicia to guide a person removing it.

The skin protective device of the invention is of a strip of relatively rigid material more resistant to cutting than the skin, such as foil or plastic to act as a protective barrier to underlie a bandage. It is severable from a roll and by reason of its flexibility, it can be adapted to conform to the general contour of the body. The strip is substantially flat and thin so that it does not injure the skin when forced against it by the bandage. The strip is provided with a surface covering that is compatible with the skin when pressed against it for a prolonged period. The device is sized to the appropriate length for the particular dressing by simply cutting the strip so that it is somewhat longer than the dressing, that is, so that the opposite ends extend outwardly from beneath the bandage.

In accordance with these and other objects which will become apparent hereinafter, the instant invention will now be described on reference to the accompanying drawings in which:

DESCRIPTION OF THE DRAWINGS

FIG. 1 is a view of the device applied to the leg of a wearer beneath a bandage;

FIG. 2 is a view of the device applied beneath a bandage on the arm of a wearer;

FIG. 3 is a plan view of the device which has been partially broken away to illustrate the details of the invention;

FIG. 4 is a view in cross-section taken on the plane indicated by the line 4—4 of FIG. 3; and FIG. 5 is a perspective view of a dispenser for the protective barrier shown in a rolled condition.

DETAILED DESCRIPTION OF THE PREFERRED EMBODIMENT

Referring to the drawings and particularly to FIG. 1, a bandage 11 is shown about the leg 12 of a wearer. Beneath the bandage there is the strip 14 with opposite ends 15 and 16 extending from beneath the bandage. Similarly in FIG. 2, the arm 12' of a wearer of a bandage 11' is shown. Beneath the bandage 11' there is the strip form protective barrier 14' having the opposite ends 15' and 16' extending from beneath the bandage. It is thus seen that the ends of the strip are visible to a person who would remove the bandage. Along the strip there is a center indicia line 17 to guide the person removing the bandage so that the tool which is being used does not injure the skin of a wearer. The user simply cuts along the bandage keeping close to the indicia line 17 so that his tool will not hit the skin without first contacting the barrier protectively covering the skin. As seen more clearly in FIG. 3, the barrier strip 14 is composed of a length of relatively rigid material 18 such as a strip of foil or bendable, pliable plastic. It has opposite edges 20 and 22 which are generally parallel to one another. The strip is encased in a wrap generally designated by the numeral 31. The strip form protective device 14 is composed of the interior foil strip 18 and, exteriorly, by a wrap of adhesive tape portions 35 and 37, in a preferred embodiment. The adhesive tape may be a single wide strip folded on itself as at 37 so that the ends 39 and 41 adhere together forming the wrap of the device and encapsulating the interior barrier 18. In an alternative embodiment the wrap portion may cover only one face of the foil where it contacts the skin.

In use, on reference to the indicia strip, when a bandage is to be removed, as in FIG. 1 or FIG. 2, the person implementing the tool for use in removal, merely uses the indicia 17 as a guide to cut the bandage and can be sure that since this is along the centerline, there is a protective barrier between the cutting tool and the skin of the bandaged person.

Referring to FIG. 5, the barrier strip may be in the form of a roll 41 within a housing 43 having an opening 45 so that the terminal end 47 may be removed from it.

It is thus seen that the skin protective device comprises a protective plate encased in adhesive tape or other material with one of the outer main surfaces having an indicia line centrally therealong to assist in removal of the bandage applied on top of the skin protective device.

The strip may be of plastic or metal such as aluminum foil, for example, 38 gauge. There may be various widths provided from about 2 inches to about 12 inches, as desired. There may be various thicknesses provided generally less than 0.015 inches, as desired. Furthermore, the device may be furnished without indicia, as desired.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

I claim:

1. A thin, flexible foil strip for use on a body member able to follow all skin contours used in connection with pressure gradient type bandages, said strip being not so rigid as to interfere with the function of the bandage, to act as a barrier when said bandage is cut away with a cutting tool upon removal, said device comprising:
   a flat, thin, bendable cut resistant foil strip, said strip having substantially parallel side edges that are smooth & non-cutting, a pair of flat main surfaces and a first and a second end;
   a wrap fixedly secured to at least one of said strip main surfaces, said wrap having a pair of main surfaces and having wrap edges which extend beyond said strip side edges to provide a compatible contact with the skin;
   said device being adapted to be severed by cutting so that a length, longer than a bandage length when in position on the body member, may be positioned under a bandage with said first and second ends extending from beneath said bandage protectively overlying the skin of a wearer.

2. The device as set forth in claim 1, further comprising centrally located indicia extending longitudinally along said device, said indicia marked on a main surface of said wrap to indicate the center of said strip when cutting away said bandage.

3. The device as set forth in claim 1, wherein said strip is of metallic foil material.

4. The device as set forth in claim 1, wherein said wrap is secured to the strip surfaces by adhesive means.

5. The device as set forth in claim 1, wherein said wrap is of adhesive tape material.

6. The device as set forth in claim 1, wherein said strip is of a foil material of a gauge of about 38.

7. The device as set forth in claim 2, wherein said strip is of a metallic foil material.

8. The device as set forth in claim 2, wherein said wrap is secured to the strip main surfaces by adhesive means.

9. A method of applying a compression type bandage to a body member and removing said bandage with reduced pain and injury, said method comprising:
   (a) cutting a thin flat elongated strip having a relatively cut-resistant inner foil and a skin-contacting surface covering means to a length greater than the length of an area on the body member to be covered by said bandage;
   (b) applying said strip to said member along a longitudinal axis of said body member in a position such that said ends will protrude from the ends of said bandage;
   (c) applying said bandage over said strip so that said strip forms a barrier between said skin and a cutting tool along a proposed cutting line for cutting through said bandage;

(d) removing said bandage by running a cutting tool along the longitudinal axis of the body member which is covered by said strip and said bandage such that the cutting tool severs the bandage without severing the strip or the patient's skin.

10. The method according to claim 9 further including applying said strip with a longitudinally marked center line indicia so that said indicia faces outwardly and provides an indication of said proposed cutting line to ensure that said foil will underlie said cutting tool during said cutting and protect said skin.

11. A barrier strip for applying beneath a compression type bandage on a body member to shield the skin from a cutting tool when cutting away said bandage, said strip comprising:

(a) an elongate, thin, flat, flexible, cut-resistant foil means, said foil means having substantially parallel smooth and non-cutting side edges and a pair of flat main surfaces;

(b) covering means affixed to at least one of said flat main surfaces and extending beyond said side edges to provide a compatible skin contacting surface on said strip;

(c) said strip having a length greater than the length of said bandage when in position on said body member and adapted for severing to a length such that it may be positioned beneath said bandage with first and second ends extending beyond the ends of said bandage when in place on said body member; wherein said strip is sufficiently flexible to conform to the contours of said body member and said strip is sufficiently thin and flat and compatible with said skin to be forced against said skin by said bandage for prolonged periods without injury to said skin.

12. The barrier strip according to claim 11, in which said covering means completely envelopes said foil means.

13. The barrier strip according to claim 12 including indicia located on one of said main surfaces and extending axially substantially along a center line of said strip for indicating the center of said strip to aid in cutting through said bandage directly above said strip to ensure protection from said cutting tool.

14. The barrier strip according to claim 11 in roll form in dispenser means for pulling out and cutting a strip to length as required.

15. The barrier strip according to claim 12 in roll form in dispenser means for pulling out and cutting a strip to length as required.

16. The barrier strip according to claim 13 in roll form in dispenser means for pulling out and cutting a strip to length as required.

* * * * *